US012569378B2

(12) United States Patent
Lindsay

(10) Patent No.: US 12,569,378 B2
(45) Date of Patent: Mar. 10, 2026

(54) RESPONSIVE ABSORBENT ARTICLES

(71) Applicant: Kimberly-Clark Worldwide, Inc., Neenah, WI (US)

(72) Inventor: Stephen M. Lindsay, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 450 days.

(21) Appl. No.: 17/917,319

(22) PCT Filed: Apr. 30, 2020

(86) PCT No.: PCT/US2020/030609
§ 371 (c)(1),
(2) Date: Oct. 6, 2022

(87) PCT Pub. No.: WO2021/221640
PCT Pub. Date: Nov. 4, 2021

(65) Prior Publication Data
US 2023/0148342 A1 May 11, 2023

(51) Int. Cl.
*A61F 13/53* (2006.01)

(52) U.S. Cl.
CPC .. *A61F 13/53* (2013.01); *A61F 2013/530481* (2013.01)

(58) Field of Classification Search
CPC .......... A61F 13/47263; A61F 13/47236; A61F 13/53; A61F 2013/530481; A61F 2013/15146; A61F 13/539; A61F 2013/53908; A61F 2013/53925
See application file for complete search history.

(56) References Cited

U.S. PATENT DOCUMENTS 5,782,787 A 7/1998 Webster
5,865,824 A * 2/1999 Chen .................. A61F 13/5323 604/385.12
6,146,367 A 11/2000 Otsubo et al.
7,491,864 B2 2/2009 Nishizawa et al.
7,847,145 B2 12/2010 Kurita et al.
8,225,729 B2 7/2012 Macdonald et al.
8,267,910 B2 9/2012 Perneborn
9,173,784 B2 11/2015 Hippe et al.
(Continued)

FOREIGN PATENT DOCUMENTS

EP 0804916 A1 11/1997
EP 0779065 B1 3/2003
(Continued)

OTHER PUBLICATIONS

International Search Report and Written Opinion for Patent Application No. PCT/US2020/030609 mailed Jan. 27, 2021; 13 pp.
(Continued)

*Primary Examiner* — Susan S Su
*Assistant Examiner* — Erin A Kim
(74) *Attorney, Agent, or Firm* — Armstrong Teasdale LLP

(57) ABSTRACT

Described herein are responsive absorbent articles. The responsive absorbent articles are capable of producing unique topographies and features upon wetting that add or enhance functionality as compared to conventional absorbent articles. Compositions and methods described herein are useful in a variety of absorbent products.

20 Claims, 11 Drawing Sheets

(56) References Cited

U.S. PATENT DOCUMENTS

2003/0125698 A1* 7/2003 Ruman ................. A61F 13/496
604/385.28
2008/0254263 A1 10/2008 Yasui et al.
2014/0303582 A1* 10/2014 Wright ............. A61F 13/15658
156/60
2018/0193517 A1* 7/2018 Feldkamp ............... A61F 13/53
2021/0161731 A1* 6/2021 Van Malderen ...... A61F 13/515

FOREIGN PATENT DOCUMENTS

EP 3016624 B1 10/2018
WO 2018119472 A1 6/2018

OTHER PUBLICATIONS

"Diaper tech: Inspired by babies;" New Scientist Live; Jan. 25, 2017; available at https://www.newscientist.com/article/mg23331101-000-diaper-tech/; last visited Oct. 3, 2022; 6 pp.

* cited by examiner

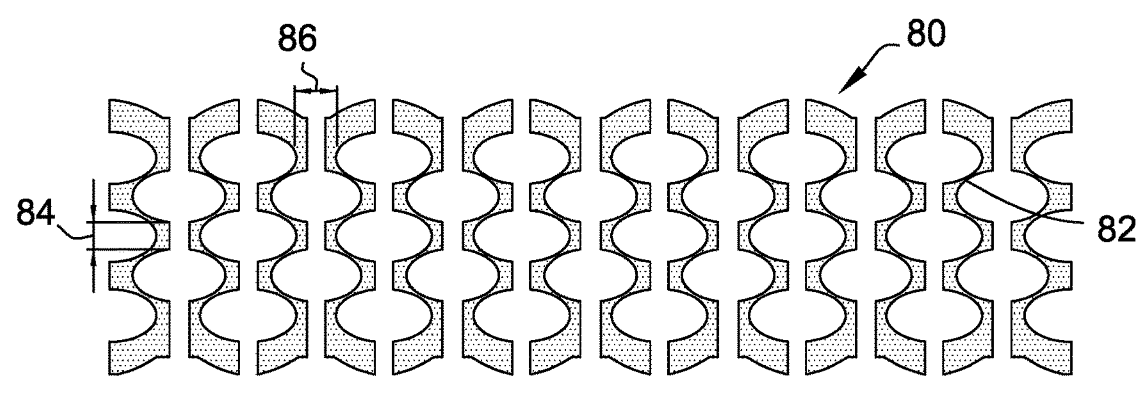
FIG. 9A
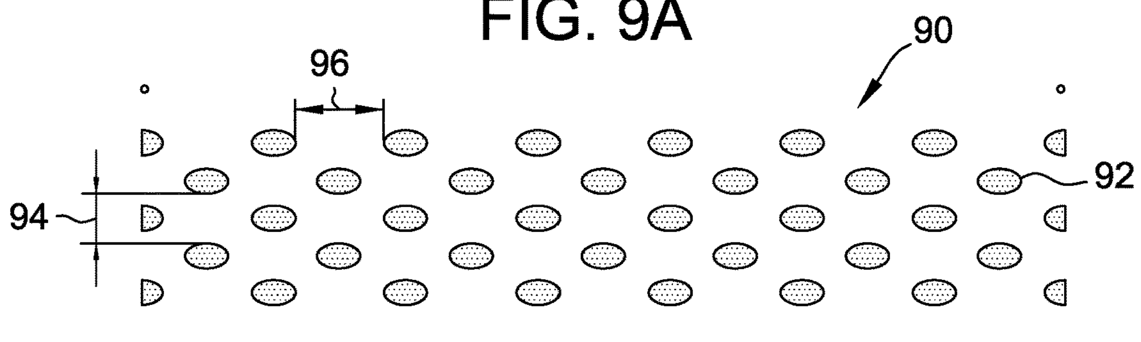
FIG. 9B
FIG. 9C
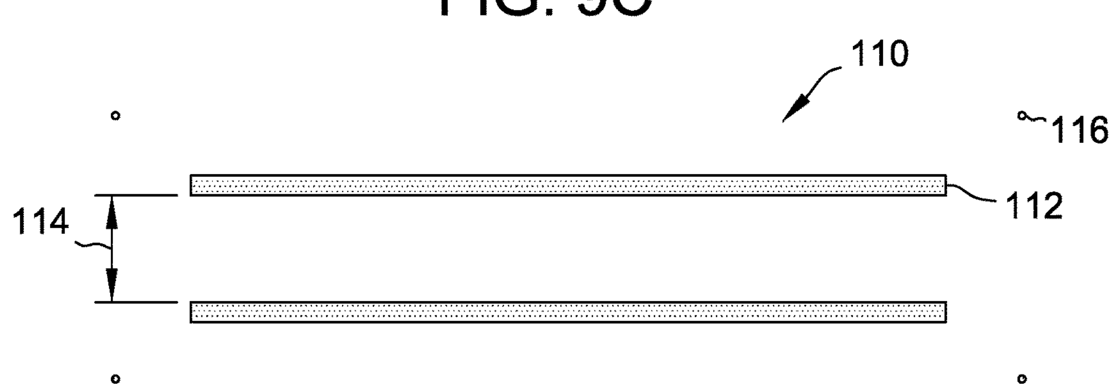
FIG. 9D

RESPONSIVE ABSORBENT ARTICLES

CROSS-REFERENCE TO RELATED APPLICATIONS

This application is a U.S. National Phase Application of International Patent Application No. PCT/US2020/030609, filed Apr. 30, 2020, the contents of which are hereby expressly incorporated by reference in their entirety.

FIELD OF DISCLOSURE

The present disclosure is directed to responsive absorbent articles. The responsive absorbent articles are capable of producing unique topographies and features upon wetting that add or enhance functionality as compared to conventional absorbent articles. Compositions and methods in accordance with the present disclosure are useful in a variety of absorbent products.

BACKGROUND

Superabsorbent materials (SAMs) are three-dimensional networks that can absorb and retain water (or other aqueous media) and physiological fluids such as urine and blood more than hundreds of times of their own dry weight, typically depending on the ionic concentration of the aqueous solution. SAMs have applications in a variety of fields, including medicine, construction, personal care products, biomaterials, biosorbents, and agriculture. SAMs were industrially developed in Japan and USA in the early 1980s for hygienic applications. It was found that SAMs had the potential to replace fluff, making their use in hygienic products such as baby diapers and feminine napkins cost effective.

Some superabsorbent materials are unique in that they swell significantly in the plane, in addition to swelling in the z-direction. The in-plane swelling is primarily in the cross-machine direction (CD), although it may also be in the machine direction (MD).

One example of superabsorbent materials with directional swelling are Flexible Reinforced On-line Development is Outstanding (FRODO) absorbent materials. These materials have been described previously, for example, in U.S. Pat. Nos. 6,362,389, 6,231,557, and 6,682,512. The in-plane swelling has been known to cause wrinkling or buckling of absorbent products and therefore has been considered a major barrier for development of products with FRODO-like absorbents.

As realized herein, however, these planar swelling properties are a moisture-triggered response that can be harnessed to create channels and/or additional void volume to move fluid for better distribution and faster intake, or larger pockets to trap solids. Controlled responsive topography could also be used to reduce the effective compressive stiffness, and/or to create body-conforming topography for comfort and reduced leakage. This is a new area of development in products containing FRODO-like absorbents.

Responsive topography has several advantages over permanent topography. Materials with responsive topography are more efficiently packaged in a flat state because the topography appears only when needed. Also, compressive forces in production or packing that typically compress or destroy permanent topographical features would have no such effect on responsive topographical features because the features are not present in production or packaging.

Attempted uses of materials with directional swelling in absorbent articles are known in the art. As one representative example, U.S. Pat. No. 5,865,824 discloses absorbent articles comprising a multifunctional transfer layer. The multifunctional transfer layer comprises a stability layer and an expansion layer heterogeneously attached to said stability layer. This expansion layer swells in-plane more than the stability layer to create functional topography. However, these absorbent articles are readily distinguishable from the absorbent articles disclosed herein. First, the absorbent core of U.S. Pat. No. 5,865,824 is not a material that swells in-plane. Rather, it is a conventional absorbent material and, instead, the additional expansion layer, which is part of the multifunctional transfer layer, swells in-plane. Second, the mechanism of responsive absorption is different. The expansion layer of U.S. Pat. No. 5,865,824 expands according to the same principle as creped tissue; the material only expands in pockets between selective attachment points per relaxation of pre-applied topography. In contrast, the entire SAMS of the absorbent articles described herein expand due to their inherent properties of in-plane swelling, and selective attachment points prevent expansion in certain directions. Third, the heights of ridges exhibited by the responsive absorbent articles of U.S. Pat. No. 5,865,824 are typically an order of magnitude lower than the heights of ridges exhibited by the absorbent articles described herein. These differences, taken together, lead to several advantages of the present responsive absorbent articles, including enhanced performance.

Disclosed herein are novel responsive absorbent articles and consumer products including responsive absorbent articles. The second intake times of these articles and products can be dramatically reduced from the first intake times, thereby enhancing distribution and reducing rewet.

Upon insult, the responsive absorbent articles disclosed herein leverage the force of expanding SAMs to trigger a shape change that adds or enhances functionality. For example, void space or channels can be created within the absorbent structure to enhance intake speed, distribution, and/or solid material capture. In consumer products including these responsive absorbent articles, such as diapers, these functionalities and enhanced properties could impact how the consumer products contain biological materials, such as runny bowel movements (BMs).

Compositions and methods in accordance with the present disclosure are useful in a variety of absorbent products.

BRIEF DESCRIPTION OF THE DISCLOSURE

In one embodiment of the present disclosure, provided herein is an absorbent article. The absorbent article includes an absorbent core and a stability layer. The absorbent core is heterogeneously attached to the stability layer, and upon wetting, the absorbent core swells in a lateral direction by at least about 20% such that the wetted absorbent core presents a responsive topography feature in a location where the absorbent core is not heterogeneously attached to the stability layer.

In another embodiment of the present disclosure, provided herein is a method of producing an absorbent article. The absorbent article includes an absorbent core and a stability layer. The absorbent core is heterogeneously attached to the stability layer, and upon wetting, the absorbent core swells in a lateral direction by at least about 20% such that the wetted absorbent core presents a responsive topography feature in a location where the absorbent core is not heterogeneously attached to the stability layer. The method includes heterogeneously coupling the absorbent core to the stability layer.

In yet another embodiment of the present disclosure, provided herein is a use of an absorbent article. The absorbent article includes an absorbent core and a stability layer. The absorbent core is heterogeneously attached to the stability layer, and upon wetting, the absorbent core swells in a lateral direction by at least about 20% such that the wetted absorbent core presents a responsive topography feature in a location where the absorbent core is not heterogeneously attached to the stability layer. The use of the absorbent article is in a consumer product.

BRIEF DESCRIPTION OF THE DRAWINGS

FIG. 9A is an exemplary embodiment of a pattern mask in accordance with the present disclosure that was prepared by modifying the pattern mask of FIG. 7A.

FIG. 9B is an exemplary embodiment of a top side mask in accordance with the present disclosure for applying adhesive in the pattern mask of FIG. 9A.

FIG. 9C is an exemplary embodiment of a pattern mask in accordance with the present disclosure that was prepared by modifying the pattern mask of FIG. 3C.

FIG. 9D is an exemplary embodiment of a top side mask in accordance with the present disclosure for applying adhesive in the pattern mask of FIG. 9C.

DETAILED DESCRIPTION OF THE DISCLOSURE

Figure 1A:
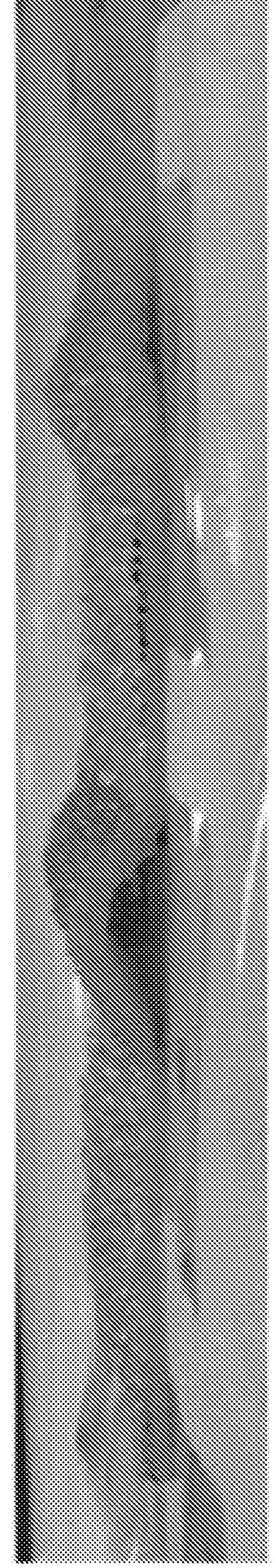
FIG. 1A is an exemplary embodiment of an absorbent article in accordance with the present disclosure that shows buckling of the absorbent article at 30 seconds.

Generally speaking, the present disclosure relates to multiple embodiments of novel responsive absorbent articles that include an absorbent core that is heterogeneously attached to a stability layer. In many embodiments, the absorbent core reacts upon wetting to swell significantly in a lateral direction. This swelling presents responsive topography, such as a responsive topography feature, in a location where the absorbent core is not heterogeneously attached to the stability layer. Responsive topographies produced in this manner increase the overall performance of the responsive absorbent articles in a product, such as an absorbent product for example. The responsive absorbent articles may be in one or more various forms in accordance with the present disclosure and may be attached to the stability layer with one or more desirable patterns.

In many embodiments, the responsive absorbent articles according to the present disclosure are thin, flat, and flexible when dry. Upon insult, within a matter of seconds, the absorbent material topography changes in a controlled manner to create an array of hills and valleys that rapidly intake and distribute fluid throughout the product. Thus, topographical features and functionalities occur only after insult. The topographical features reduce intake time, especially for subsequent insults, by preventing oversaturation of the target zone. Further, the newly formed channels rapidly control fluid. In many embodiments, including in absorbent products such as diapers, the topography can also be designed to enable rapid capture fluids, such as runny BMs for example.

In many embodiments, the responsive absorbent articles according to the present disclosure include a stabilized absorbent material containing a bound SAM. When insulted, the SAM swells and expands preferentially in the direction(s) of least resistance to expansion, typically the direction(s) of lowest strength. If the material is able to expand readily in the CD direction, the material will tend to buckle in the CD direction, creating ridges generally aligned with the machine direction. FRODO materials containing elastic fibers are one example, although any similar suitable material is possible, in some cases expanding greater than about 70% in the x-y plane, primarily in the CD direction.

The absorbent core may be heterogeneously attached to the stability layer in any operable manner. In some embodiments, the absorbent core and stability layer may be heterogeneously attached to each other by attachment means such as adhesives, sonic bonds, thermal bonds, or any other attachment means known in the art.

It is readily apparent that the attachment means described herein may also be employed to interconnect and assemble together other components in products containing the responsive absorbent articles according to the present disclosure.

In some specific embodiments of the present disclosure, the absorbent core is heterogeneously attached to the stability layer according to a pattern comprising a feature selected from the group consisting of a continuous feature, a discrete feature, an array of continuous features, an array of discrete features, a feature formed in a negative space between a plurality of features, and combinations thereof. In some embodiments, the continuous feature is selected from the group consisting of full length MD or CD features, strips, stripes, ripples, and combinations thereof. In some embodiments, the discrete feature is selected from the group consisting of shapes, circles, ovals, squares, rectangles, triangles, diamonds, geometric shapes, modified geometric shapes, asymmetric shapes, shapes created in a negative space between a plurality of shapes, and combinations thereof.

In some embodiments, the absorbent core is heterogeneously attached to the stability layer according to a pattern comprising shapes selected from the group consisting of circles, ovals, squares, rectangles, triangles, diamonds, geometric shapes, modified geometric shapes, asymmetric shapes, shapes created in a negative space between a plurality of shapes, and combinations thereof.

In some embodiments, at least two features are separated by at least ⅛ inches. In some embodiments, at least two features are separated by at least ¼ inches. In some embodiments, at least two features are separated by at least ⅜ inches. In some embodiments, at least two features are separated by at least ½ inches. In some embodiments, at least two features are separated by at least ⅝ inches. In some embodiments, at least two features are separated by at least ¾ inches. In some embodiments, at least two features are separated by at least ⅞ inches. In some embodiments, at least two features are separated by at least 1 inch. In some embodiments, at least two features are separated by at least 1.5 inches. In some embodiments, at least two features are separated by at least 2 inches. In some embodiments, at least two features are separated by at least 2.5 inches. In some embodiments, at least two features are separated by at least 3 inches.

In some embodiments, at least two of the features are connected to a degree selected from the group consisting of fully connected, partially connected, and not connected. In some embodiments, at least two of the features are connected. In some embodiments, at least two of the features are not connected.

In some embodiments, the majority of the features are connected. In some embodiments, the minority of the features are connected.

In some embodiments, the majority of the features are not connected. In some embodiments, the minority of the features are not connected.

In some embodiments, the absorbent core comprises a material selected from the group consisting of a stabilized superabsorbent material, a superabsorbent material bound in a nonwoven web, a FRODO material, a coform superabsorbent material, a superabsorbent airlaid, a superabsorbent foam, a superabsorbent material laminated to a nonwoven facing that is stretchable in-plane, and combinations thereof.

The superabsorbent material may comprise conventional superabsorbent materials known to impart desirable properties to absorbent articles. In some embodiments, the superabsorbent material comprises a polymer comprising a polymerizable monomer selected from the group consisting of 2-acrylamido-2-methylpropane sulfonic acid, methacrylate monomers with tethered sulfate groups, salts of vinyl-linker-acid units, vinylic sulfate monomers, acrylic acids, vinyl sulfonic acids, vinyl phosphoric acids, partially hydrolyzed maleic anhydrides, sodium alginate, chitosan salt, modified starches, and combinations thereof. In some embodiments, the superabsorbent material comprises a polymer selected from the group consisting of polyacrylic acid (PAA), poly(2-acrylamido-2-methyl-1-propanesulfonic acid) (polyAMPS), and combinations thereof.

In some embodiments, the superabsorbent material has a substantial degree of neutralization. In some embodiments, the superabsorbent material has a degree of neutralization greater than about 50%. In some embodiments, the superabsorbent material has a degree of neutralization greater than about 60%. In some embodiments, the superabsorbent material has a degree of neutralization greater than about 70%. In some embodiments, the superabsorbent material has a degree of neutralization greater than about 80%. In some embodiments, the superabsorbent material has a degree of neutralization greater than about 90%. In some embodiments, the superabsorbent material has a degree of neutralization greater than about 95%. In some embodiments, the superabsorbent material has a degree of neutralization greater than about 99%.

In some embodiments, the absorbent core may further comprise a crosslinker. Suitable crosslinkers include conventional crosslinkers. In some embodiments, the crosslinker comprises at least two double bonds.

In some embodiments, the crosslinker is selected from the group consisting of methylene(bis) acrylamide (MBAA), poly(ethylene glycol diacrylate) (PEGDA), ethylene glycol diacrylate (EGDA), ethylene glycol dimethacrylate (EGDMA), poly(ethylene glycol dimethacrylate) (PEGDMA), and combinations thereof. In some embodiments, the crosslinking density of the absorbent article is in the range of from about 0.1 mol % to about 1 mol %. In some embodiments, the crosslinking density of the absorbent article is in the range of from about 0.2 mol % to about 1 mol %.

In some embodiments, the stabilizing material of the stabilized superabsorbent material may be selected from any stabilizing material known in the art. In some embodiments, the stabilizing material of the stabilized superabsorbent material is a nonwoven webs. Nonwoven webs include continuous spun fibers (as in coform), wood pulp fibers, synthetic staple fibers, elastic fibers, regenerated cellulose fiber, binder fibers, and combinations thereof. Nonwoven webs may further include latex or other binder chemistries or other chemical treatments. The structures of nonwoven webs may be modified according to a physical post-treatment such as calendaring, ring-rolling, creping, embossing, rush transfer, heating, and combinations thereof.

In many embodiments, upon wetting, the absorbent core swells significantly in a lateral direction. In some embodiments, upon wetting, the absorbent core swells in a lateral direction by at least about 10%. In some embodiments, upon wetting, the absorbent core swells in a lateral direction by at least about 15%. In some embodiments, upon wetting, the absorbent core swells in a lateral direction by at least about 20%. In some embodiments, upon wetting, the absorbent core swells in a lateral direction by at least about 25%. In some embodiments, upon wetting, the absorbent core swells in a lateral direction by at least about 30%. In some embodiments, upon wetting, the absorbent core swells in a lateral direction by at least about 35%. In some embodiments, upon wetting, the absorbent core swells in a lateral direction by at least about 40%. In some embodiments, upon wetting, the absorbent core swells in a lateral direction by at least about 45%. In some embodiments, upon wetting, the absorbent core swells in a lateral direction by at least about 50%. In some embodiments, upon wetting, the absorbent core swells in a lateral direction by at least about 55%. In some embodiments, upon wetting, the absorbent core swells in a lateral direction by at least about 60%. In some embodiments, upon wetting, the absorbent core swells in a lateral direction by at least about 65%. In some embodiments, upon wetting, the absorbent core swells in a lateral direction by at least about 70%. In some embodiments, upon wetting, the absorbent core swells in a lateral direction by at least about 75%. In some embodiments, upon wetting, the absorbent core swells in a lateral direction by at least about 80%.

In some embodiments, upon wetting, the absorbent core swells in a lateral direction by at least about 10%. In some embodiments, upon wetting, the absorbent core swells in a lateral direction by at least about 20%. In some embodiments, upon wetting, the absorbent core swells in a lateral direction by at least about 30%. In some embodiments, upon wetting, the absorbent core swells in a lateral direction by at least about 40%. In some embodiments, upon wetting, the absorbent core swells in a lateral direction by at least about 50%.

In some embodiments, upon wetting, the absorbent core swells in a lateral direction and in a non-lateral direction selected from the group consisting of a z-direction, a vertical direction, and a direction orthogonal to the lateral plane. The amount of non-lateral swelling is immaterial provided that a significant swelling occurs in a lateral direction such that a beneficial responsive topography is produced, and provided that the non-lateral swelling does not inhibit buckling and/or formation of responsive topography.

In some embodiments, the absorbent core swells significantly in a direction selected from the group consisting of a cross machine direction, a machine direction, and combinations thereof. In some embodiments, the absorbent core swells significantly in a cross machine direction. In some embodiments, the absorbent core swells significantly in a machine direction. In some embodiments, the absorbent core swells significantly in a machine direction and a cross machine direction.

In some embodiments, the absorbent core presents a responsive topography feature within about 60 seconds of wetting. In some embodiments, the absorbent core presents a responsive topography feature within about 50 seconds of wetting. In some embodiments, the absorbent core presents a responsive topography feature within about 40 seconds of wetting. In some embodiments, the absorbent core presents a responsive topography feature within about 40 seconds of wetting. In some embodiments, the absorbent core presents a responsive topography feature within about 20 seconds of wetting. In some embodiments, the absorbent core presents a responsive topography feature within about 15 seconds of wetting. In some embodiments, the absorbent core presents a responsive topography feature within about 10 seconds of wetting. In some embodiments, the absorbent core presents a responsive topography feature within about 5 seconds of wetting.

In some embodiments, upon wetting, the absorbent core presents a responsive topography feature with a height greater than about 1 mm. In some embodiments, upon wetting, the absorbent core presents a responsive topography feature with a height greater than about 2 mm. In some embodiments, upon wetting, the absorbent core presents a responsive topography feature with a height greater than about 3 mm. In some embodiments, upon wetting, the absorbent core presents a responsive topography feature with a height greater than about 4 mm. In some embodiments, upon wetting, the absorbent core presents a responsive topography feature with a height greater than about 5 mm. In some embodiments, upon wetting, the absorbent core presents a responsive topography feature with a height greater than about 6 mm. In some embodiments, upon wetting, the absorbent core presents a responsive topography feature with a height greater than about 7 mm. In some embodiments, upon wetting, the absorbent core presents a responsive topography feature with a height greater than about 8 mm. In some embodiments, upon wetting, the absorbent core presents a responsive topography feature with a height greater than about 9 mm. In some embodiments, upon wetting, the absorbent core presents a responsive topography feature with a height greater than about 10 mm. In some embodiments, upon wetting, the absorbent core presents a responsive topography feature with a height greater than about 11 mm. In some embodiments, upon wetting, the absorbent core presents a responsive topography feature with a height greater than about 12 mm. In some embodiments, upon wetting, the absorbent core presents a responsive topography feature with a height greater than about 13 mm. In some embodiments, upon wetting, the absorbent core presents a responsive topography feature with a height greater than about 14 mm. In some embodiments, upon wetting, the absorbent core presents a responsive topography feature with a height greater than about 15 mm. In some embodiments, upon wetting, the absorbent core presents a responsive topography feature with a height greater than about 16 mm. In some embodiments, upon wetting, the absorbent core presents a responsive topography feature with a height greater than about 17 mm. In some embodiments, upon wetting, the absorbent core presents a responsive topography feature with a height greater than about 18 mm. In some embodiments, upon wetting, the absorbent core presents a responsive topography feature with a height greater than about 19 mm. In some embodiments, upon wetting, the absorbent core presents a responsive topography feature with a height greater than about 20 mm. In some embodiments, upon wetting, the absorbent core presents a responsive topography feature with a height greater than about 21 mm. In some embodiments, upon wetting, the absorbent core presents a responsive topography feature with a height greater than about 22 mm. In some embodiments, upon wetting, the absorbent core presents a responsive topography feature with a height greater than about 23 mm. In some embodiments, upon wetting, the absorbent core presents a responsive topography feature with a height greater than about 24 mm. In some embodiments, upon wetting, the absorbent core presents a responsive topography feature with a height greater than about 25 mm.

In some embodiments, upon wetting, the absorbent core presents a responsive topography feature with a height in the range of from about 1 mm to about 25 mm. In some embodiments, upon wetting, the absorbent core presents a responsive topography feature with a height in the range of from about 5 mm to about 20 mm. In some embodiments, upon wetting, the absorbent core presents a responsive topography feature with a height in the range of from about 5 mm to about 15 mm. In some embodiments, upon wetting, the absorbent core presents a responsive topography feature with a height in the range of from about 5 mm to about 10 mm.

In some embodiments, upon wetting, the absorbent core presents a responsive topography feature with a height in the range of from about 10 mm to about 25 mm. In some embodiments, upon wetting, the absorbent core presents a responsive topography feature with a height in the range of from about 10 mm to about 20 mm. In some embodiments, upon wetting, the absorbent core presents a responsive topography feature with a height in the range of from about 10 mm to about 15 mm.

In many embodiments, any responsive topography feature is suitable provided that it imparts beneficial properties to the absorbent article. In some embodiments, the responsive topography feature is selected from the group consisting of hills, ridges, bumps, dots, channels, voids, valleys, drumlins, eskers, and combinations thereof.

In many embodiments, the hills and valleys are in an arrangement selected from the group consisting of elongated, straight, bent, wavy, parallel, arrayed, discrete, linear, branched, and combinations thereof. In some embodiments, the hills and valleys have different heights. In some embodiments, the combination of hills and valleys creates channels In some embodiments, a plurality of parallel hills form a responsive topography feature between the plurality of parallel hills selected from the group consisting of valleys, channels, and combinations thereof. In some embodiments, the hills and valleys are in an arrangement comprising discrete hills isolated by valleys.

In many embodiments, the responsive topography imparts at least one beneficial property to the absorbent article. In some embodiments, the responsive topography imparts at least two beneficial properties to the absorbent article. In some embodiments, the responsive topography imparts at least three beneficial properties to the absorbent article.

In some embodiments, the responsive topography enhances distribution of fluid through the responsive absorbent material. In some embodiments, the responsive topography reduces intake time during an insult subsequent to a first insult. In some embodiments, the responsive topography prevents oversaturation of the target zone of the absorbent article. In some embodiments, the responsive topography enables capture of runny biological materials. In some embodiments, the responsive topography reduces the effective compressive stiffness. In some embodiments, the responsive topography creates body-conforming topography to increase comfort and reduce leakage.

In many embodiments, the responsive absorbent articles according to the present disclosure include a stability layer heterogeneously attached to the absorbent core. In some embodiments, upon wetting, the stability layer does not swell significantly in any direction. In some embodiments, upon wetting, the absorbent core expands more than the stability layer.

In some embodiments, the stability layer is selected from the group consisting of a liquid impervious backsheet, a spacer layer, a spunbond spacer layer, a nonwoven material, a film, and combinations thereof. In some embodiments, the stability layer is a liquid impervious backsheet. In some embodiments, the stability layer is adjacent to or bonded to the liquid impervious backsheet.

The liquid impervious backsheet can be any material known in the art. In some embodiments, the backsheet is composed of a substantially liquid impermeable material, and is typically manufactured from a thin plastic film, or other flexible liquid-impermeable material. However, polymer-wood fiber composites may also be used, or even tissue-based structures with suitable imperviousness to liquid. As used herein, the term "flexible" refers to materials which are compliant and which will readily conform to the general shape and contours of the wearer's body. The backsheet can be a polyethylene film having a thickness of from about 0.012 millimeters to 0.051 millimeters, depending upon cost constraints and strength requirements. Alternative constructions of the backsheet may comprise a woven or nonwoven fibrous web layer which has been constructed or treated to impart the desired level of liquid impermeability. For example, the backsheet may comprise a polymer film. The polymer film backsheet can also be embossed and/or matte finished to provide a more aesthetically pleasing appearance. The backsheet may optionally be composed of a vapor permeable, "breathable" material which permits vapors to escape from the absorbent structure while still substantially preventing liquid exudates from passing through the backsheet. For example, the backsheet can comprise a microporous, polymer film, or a nonwoven fabric that has been coated or otherwise treated to impart desired levels and combinations of liquid impermeability and vapor permeability. The shape and size of the backsheet are determined by the size and contour of the absorbent article and by the particular design selected. When used in a diaper or similar article, for example, the backsheet may have a generally T-shape, a generally I-shape or a modified hourglass shape, and may extend beyond the terminal edges of the article by a selected distance, e.g., 1.3 centimeters to 2.5 centimeters (0.5 to 1.0 inch).

In some embodiments, the stability layer comprises a material selected from the group consisting of a polymer, polyethylene, a plastic, a thin plastic film, a flexible liquid-impermeable material, a polymer-wood fiber composite, a tissue-based structure, and combinations thereof.

In some embodiments, the absorbent article is substantially flexible before wetting and substantially rigid after wetting.

The responsive absorbent articles according to the present disclosure may be produced according to any suitable means.

In some specific embodiments, the responsive absorbent articles according to the present disclosure may be produced according to a method including heterogeneously coupling the absorbent core to the stability layer.

In some embodiments, the method step of heterogeneously coupling the absorbent core to the stability layer comprises forming a bond selected from the group consisting of adhesive bonds, sonic bonds, thermal bonds, and combinations thereof. In some embodiments, the method step of heterogeneously coupling the absorbent core to the stability layer comprises applying an adhesive.

In many embodiments, the adhesive is applied with a width that imparts desirable properties to the absorbent article. In some embodiments, the adhesive is applied with a width greater than about ⅛ inches. In some embodiments, the adhesive is applied with a width greater than about ¼ inches. In some embodiments, the adhesive is applied with a width greater than about ⅜ inches. In some embodiments, the adhesive is applied with a width greater than about ½ inches. In some embodiments, the adhesive is applied with a width greater than about ⅝ inches.

Absorbent articles according to the present disclosure may be used in an absorbent composite. In some embodiments, an absorbent composite comprises an absorbent article according to the present disclosure.

In some embodiments, a method of using an absorbent article according to the present disclosure comprises using the absorbent article in an absorbent composite.

Absorbent articles according to the present disclosure may be used in a consumer product. In some embodiments, a consumer product comprises an absorbent article according to the present disclosure.

In some embodiments, a method of using an absorbent article according to the present disclosure comprises using the absorbent article in a consumer product.

In some embodiments, the consumer product is selected from the group consisting of cloth products, diapers, potty training paints, feminine napkins, adult incontinence pads, adult incontinence garments, and disposable bed liners.

The consumer product comprising the absorbent article according to the present disclosure may comprise conventional product components known in the art. In some specific embodiments, the consumer product comprising the absorbent article according to the present disclosure comprises a product component selected from the group consisting of an intake layer, a body side liner, a leg elastic, a fastening system, a fastening means, a tab, an elastic thread, an insert, an adhesive band, a strap, and combinations thereof.

EXAMPLES

Without further elaboration, it is believed that one skilled in the art using the preceding description can utilize the present invention to its fullest extent. The following Examples are, therefore, to be construed as merely illustrative, and not limiting of the disclosure in any way whatsoever.

Example 1. Planar Expansion

⅜" stripes of adhesive were created by using cut post it notes as a mask and spraying a synthetic elastomer spray adhesive (Super 77) onto a piece of low density polyethylene film cut from a scientific sample bag. A strip of FRODO material (nonwoven material containing 400 gsm of SAM, with fluff pulp and thermoplastic olefinic elastomer (Vistamax) meltblown fibers that enable in-plane swelling, used throughout the Examples) was pressed over the adhesive stripes and the FRODO material was exposed to insult, to roughly saturation, with room temperature saline. A gradual buckling deformation was observed.

About 30-40% expansion was observed in the CD and about 10% was observed in the MD. Overall there was about 50% overall expansion in length (MD, CD) and area (overall). These results demonstrate that responsive topography can be controlled to the area between adhesive stripes.

Example 2. Restricted Expansion with Broad Adhesive Spacing

Figure 1B:
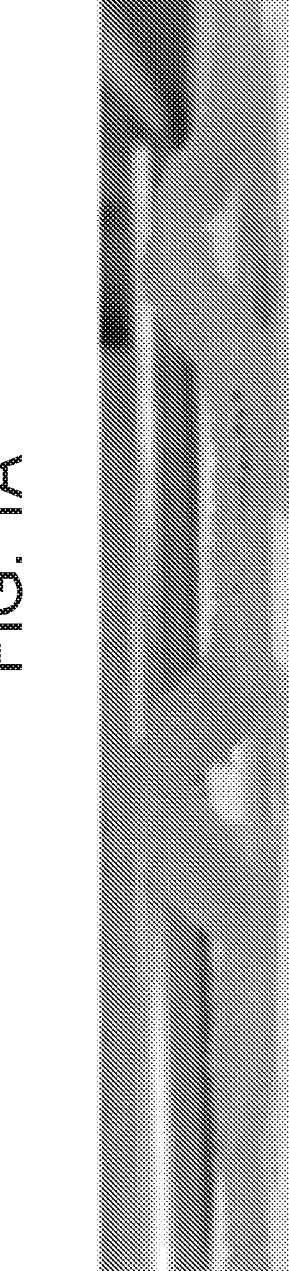
FIG. 1B is an exemplary embodiment of an absorbent article in accordance with the present disclosure that shows buckling of the absorbent article at 60 seconds.
Figure 1B:
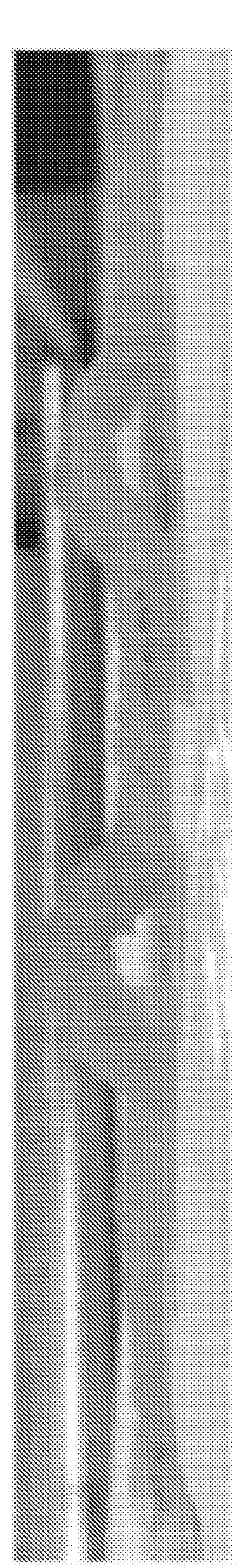
Figure 1C:
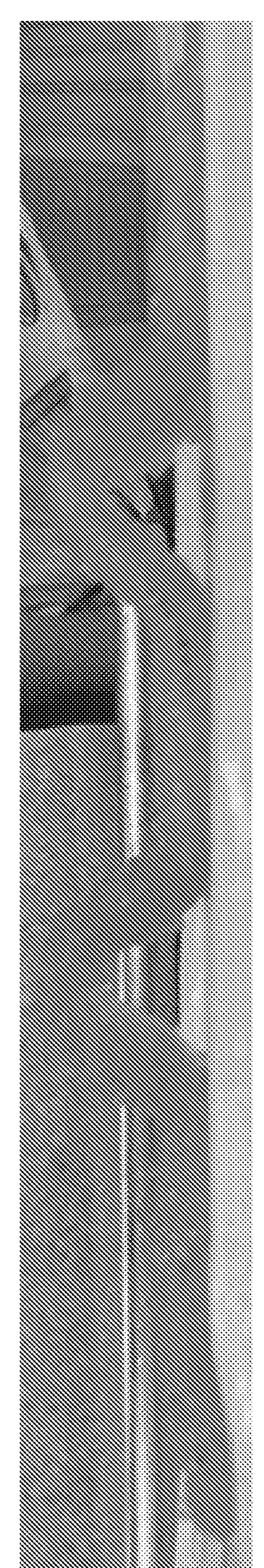
FIG. 1C is an exemplary embodiment of an absorbent article in accordance with the present disclosure that shows buckling of the absorbent article after equilibrating for a couple of minutes.

A 2" by 6" strip of FRODO material was bound to a surface with a 38" strip of adhesive at the edges and at the center. Buckling occurred in the CD in the gaps between the adhesive. Progressive formation of responsive topography was observed over time. FIG. 1A shows the response at 30 seconds, FIG. 1B shows the response at 60 seconds, and FIG. 1C shows the response after equilibrating for a couple of minutes. The controlled formation of responsive topography created topography similar to channels or ridges.

Example 3. Restricted Expansion with Narrow Adhesive Spacing

To explore the effects of adhesive spacing, a second sample was created with narrower adhesive spacing. The materials and procedures were the same as for Example 2.

Figure 2:
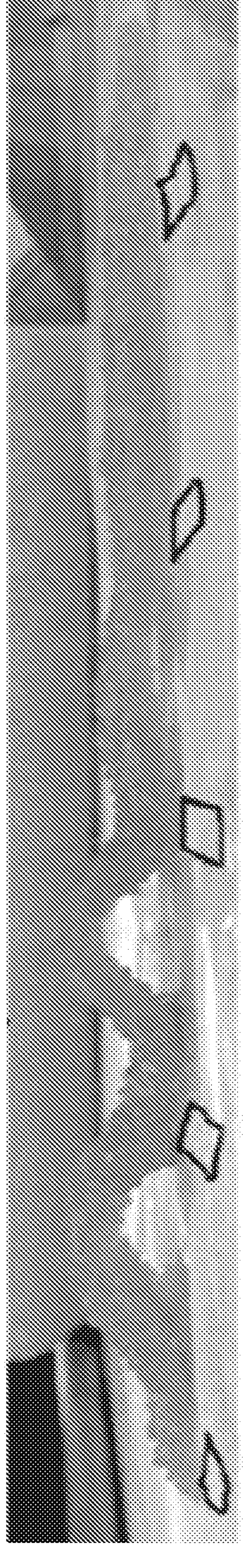
FIG. 2 is an exemplary embodiment of an absorbent article in accordance with the present disclosure. The absorbent article has relatively narrow adhesive spacing, as shown by the outlined rectangles.

As shown in FIG. 2, expansive force caused failure in two adhesive bonds on one end as the material approached maximum swell. The locations of adhesive strips are indicated by the squares below the FRODO material. These results demonstrate that the adhesive bonds at the extreme edges experience the most stress when swollen because there is not a counteracting force from neighboring buckling section.

Example 4. Channel Size

Channel size can be controlled by the spacing between the strips of adhesive that pin the FRODO material to the outer cover. Larger ridges are created by leaving a larger amount of space between strips of adhesive.

4" by 14" cores were cut out of the FRODO material. 11" by 17" paper masks were printed for adhesive patterning. The hatched regions were cut out with a blade. Three different MD line masks were made.

Figures 3A, 3B, 3C:
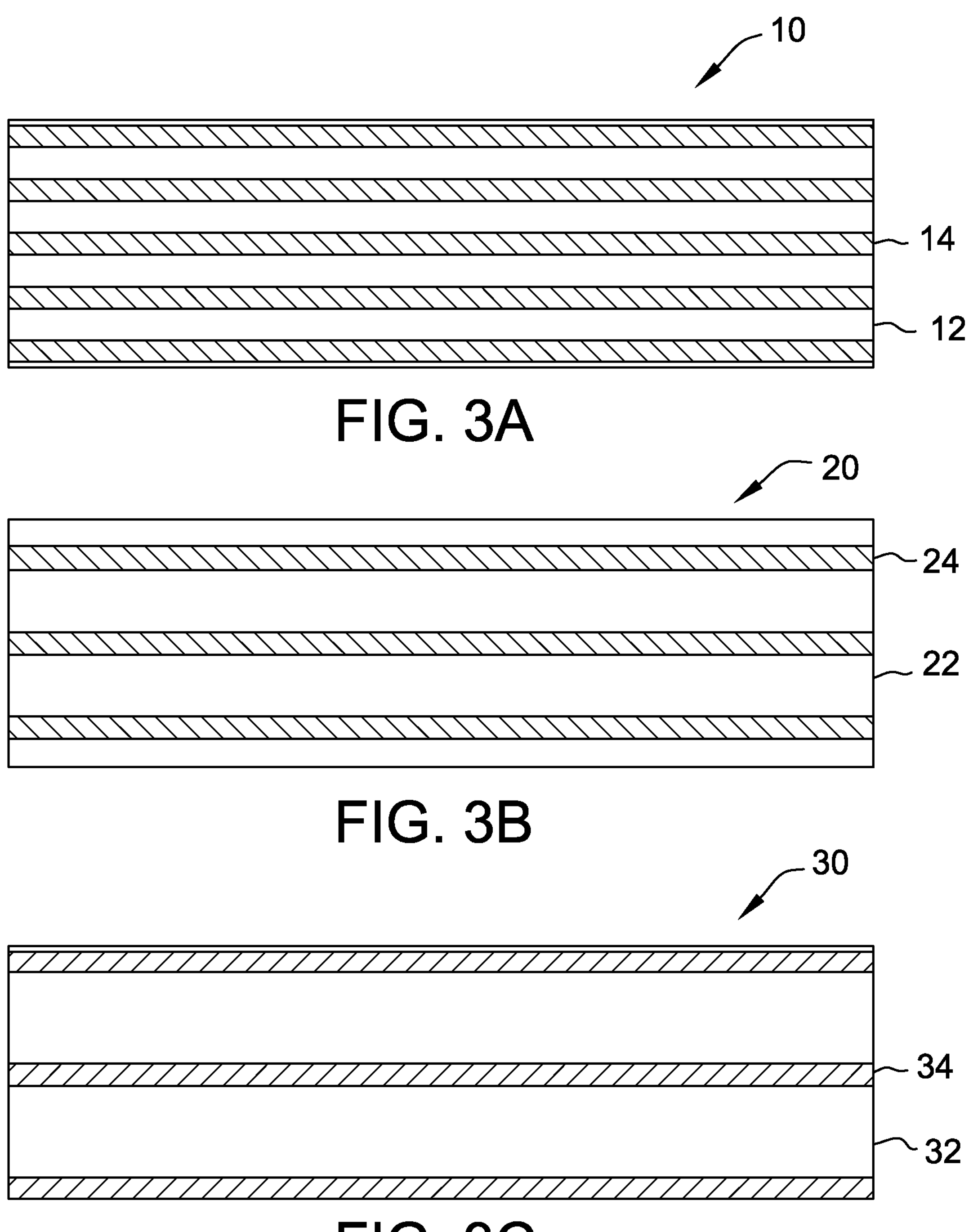
FIG. 3A is an exemplary embodiment of a MD linear pattern mask in accordance with the present disclosure.
FIG. 3B is an exemplary embodiment of a MD linear pattern mask in accordance with the present disclosure.
FIG. 3C is an exemplary embodiment of a MD linear pattern mask in accordance with the present disclosure.

Mask 3A, indicated generally at 10, is shown in FIG. 3A. Mask 3A had 0.5" gaps 12 between adhesive strips 14.

Mask 3B, indicated generally at 20, is shown in FIG. 3B. Mask 3B had 1" gaps 22 between adhesive strips 24.

Mask 3C, indicated generally at 30, is shown in FIG. 3C. Mask 3C had 1.5" gaps 32 between adhesive strips 34.

Figure 4A:
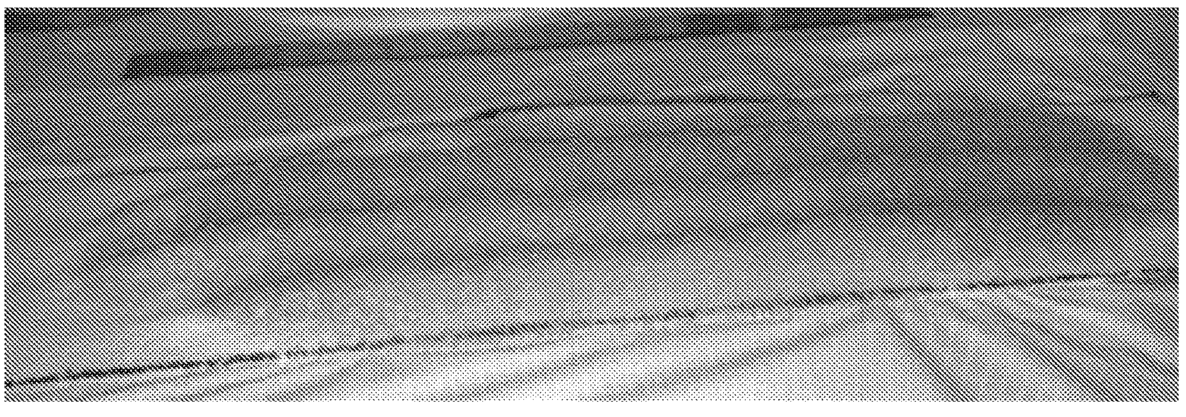
FIG. 4A is an exemplary embodiment of an absorbent article in accordance with the present disclosure. This absorbent article was made with the MD linear pattern mask of FIG. 3A.
Figure 4B:
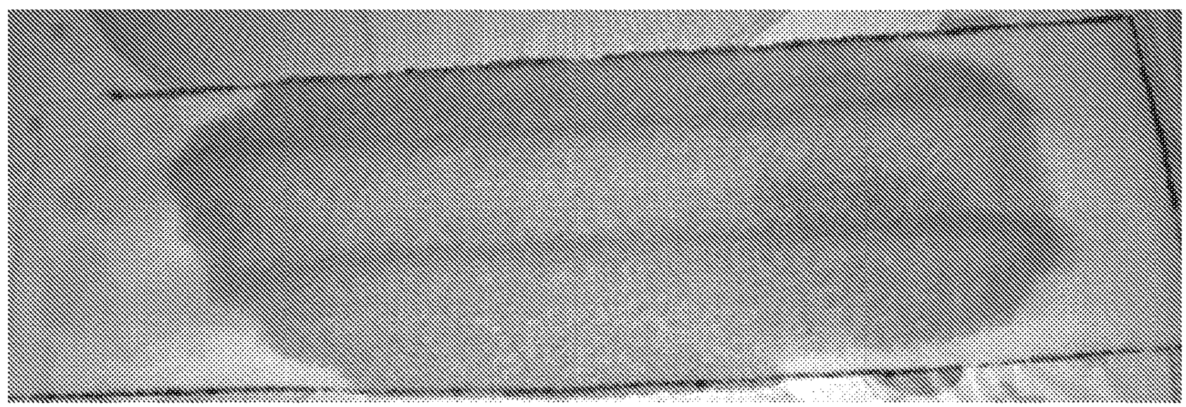
FIG. 4B is an exemplary embodiment of an absorbent article in accordance with the present disclosure. This absorbent article was made with the MD linear pattern mask of FIG. 3B.
Figure 4C:
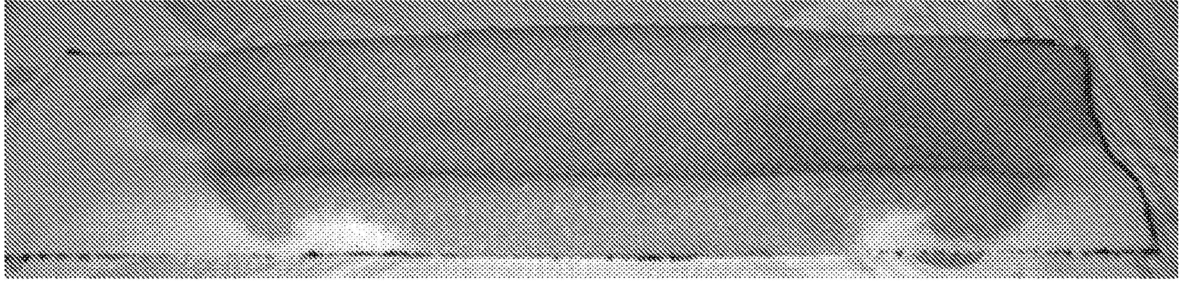
FIG. 4C is an exemplary embodiment of an absorbent article in accordance with the present disclosure. This absorbent article was made with the MD linear pattern mask of FIG. 3C.

Each mask was laid over a piece of diaper outer cover film and a thick layer of Super77 adhesive was sprayed. A core was pressed, mesh-side down, onto the adhesive/outer cover to make each test specimen. A rubber roller was used to press and smooth each core on the cover film. Each sample remained undisturbed for at least 1 hour to allow the adhesive to set. After allowing time to equilibrate, the samples were insulted with 37° C. saline, which was warmed in a microwave, by pouring the saline from a beaker. The respective swelling responses for each mask are shown in FIG. 4 and the results are summarized in Table 1. The time to move fluid was visually estimated as the earliest time that the ridges were formed enough to expect a fluid handling functionality.

TABLE 1

| Insult test results. | | | | |
|---|---|---|---|---|
| Mask | Gap Distance (inch) | Ridge Height at Full Saturation (mm) | Time to move fluid | Adhesive Failure |
| 3A | 0.5 | 6-9 | After about 25-30 seconds | At one extreme edge |
| 3B | 1 | 12-14 | Within 25 seconds | N/A |
| 3C | 1.5 | 20 | Within 15 seconds | N/A |

The data in Table 1 demonstrate that adhesive spacing is linearly correlated to ripple amplitude. If the ripples are small, the expansive force pushing against the adhesive is larger. Early on, fluid is carried in the undersides of the ridges. Subsequent insults largely travel through the valleys between hills. These designs enhance distribution of at least a second insult, and distribution could also be enhanced for further insults.

The time scale to channel formation is about 15-30 seconds. The size scale of the channel height was about 6-9 mm minimum and about 20 mm maximum. Further, for the largest gaps, gasket-like topology wase formed at the edges, which created a large bucket to hold fluid in the center.

Example 5. Diamond Patterns

Figure 5:
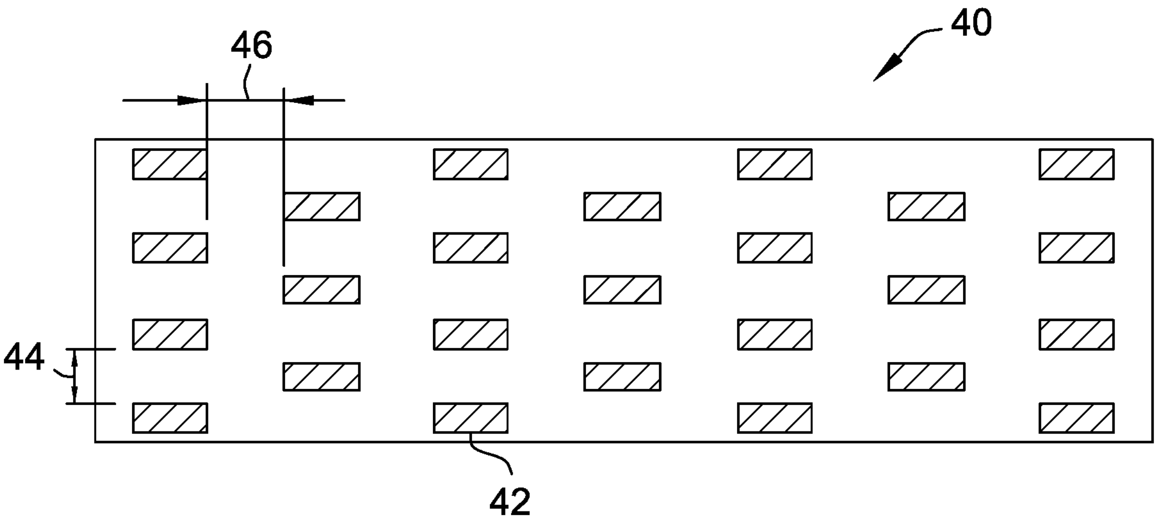
FIG. 5 is an exemplary embodiment of a diamond pattern mask in accordance with the present disclosure.

To explore the effects of pattern shape, an additional sample with rectangular bonded areas arranged in a diamond pattern was created. The materials and procedures were the same as for Example 4. The mask, indicated generally at 40, is shown in FIG. 5. The rectangles 42 are ⅜" by 1". The CD gap 44 between rectangles 12 is ¾". The MD gap 46 between rows of rectangles 12 is 1". Each row of rectangles 12 is offset to the midpoint of the neighboring rows to create a hexagonal array.

Figure 6:
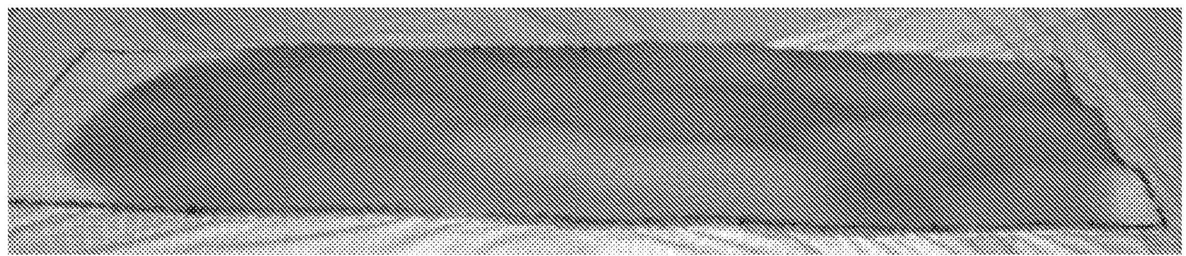
FIG. 6 is an exemplary embodiment of an absorbent article in accordance with the present disclosure. This absorbent article was made with the diamond pattern mask of FIG. 5.

The swelling responses for a FRODO material patterned with this mask (Mask 5) were determined. After about 18 seconds, fluid puddled in the interconnected MD-oriented bonded areas. This diamond-shaped network of bonded areas beneficially moved fluids in the MD, but did not restrict flow to one or two discrete lines like the linear bonded areas. The ridges produced by responsive topography eventually reached about 11-15 mm heights (FIG. 6). At full swell, some of the adhesive failed at the edges. These results demonstrated that a pattern of offset rectangular bonded areas produces MD oriented flow without restricting flow to distinct channels.

Example 6. Variations on Diamond-Based Patterns

Additional diamond-based masks were created according to the materials and procedures for Examples 4 and 5. The masks are shown in FIGS. 7A-C.

Figures 7A, 7B, 7C:
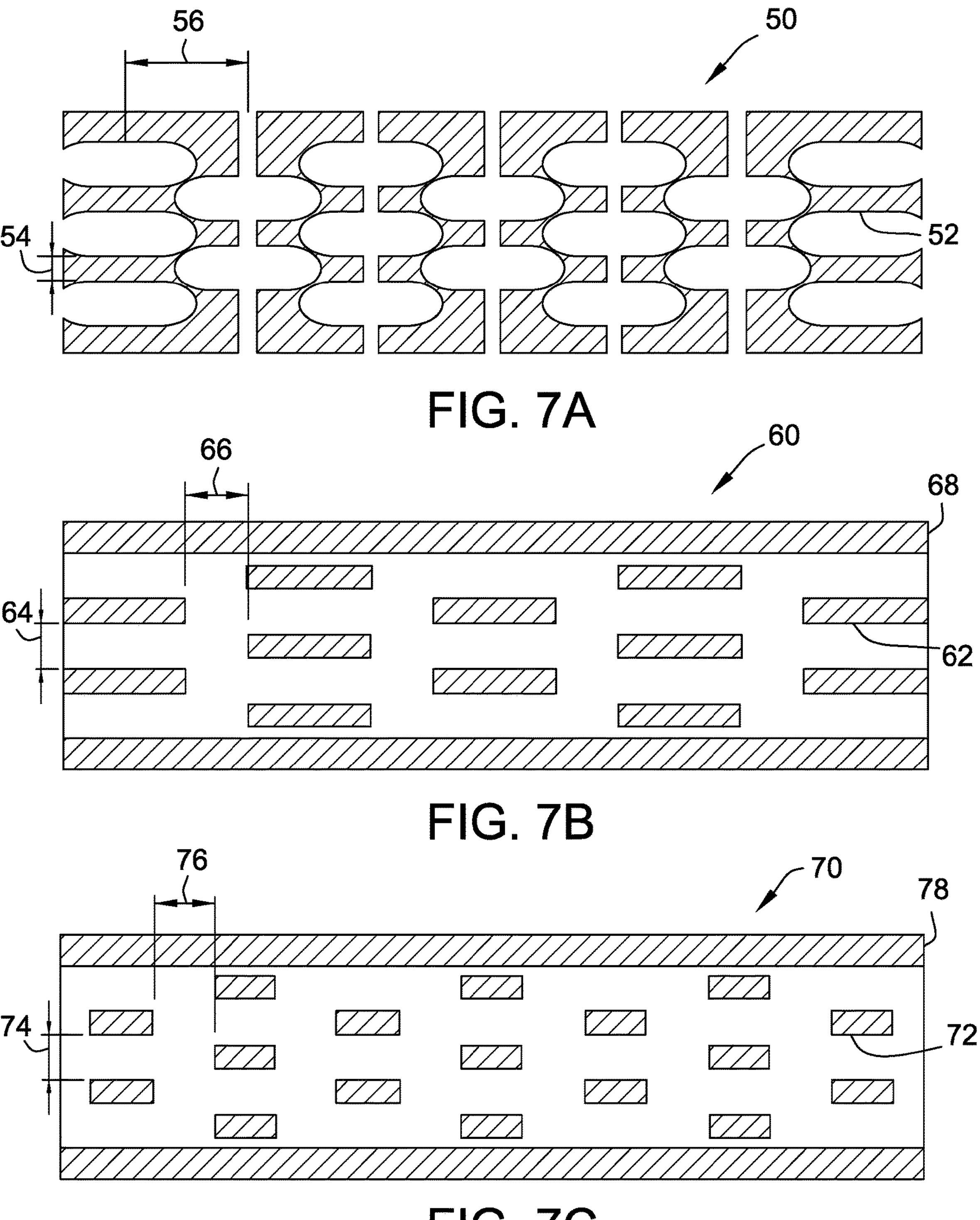
FIG. 7A is an exemplary embodiment of a varied diamond pattern mask in accordance with the present disclosure.
FIG. 7B is an exemplary embodiment of a varied diamond pattern mask in accordance with the present disclosure.
FIG. 7C is an exemplary embodiment of a varied diamond pattern mask in accordance with the present disclosure.
Figure 8A:
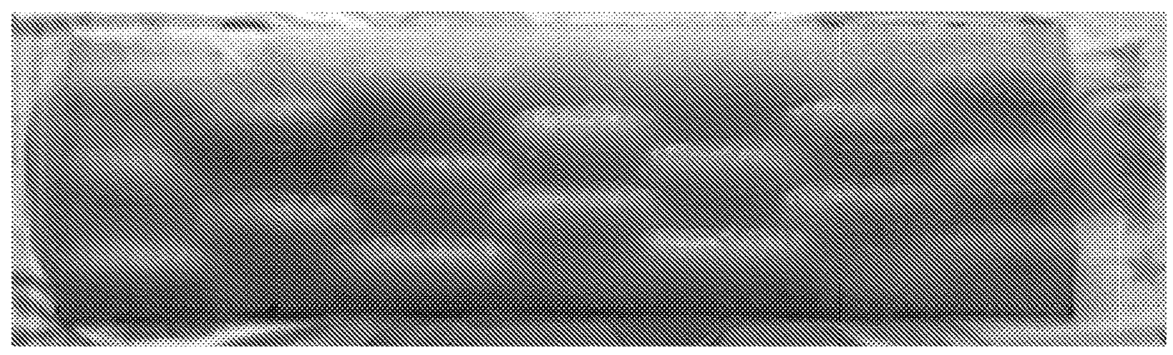
FIG. 8A is an exemplary embodiment of an absorbent article in accordance with the present disclosure. This absorbent article was made with the varied diamond pattern mask of FIG. 7A.
Figure 8B:
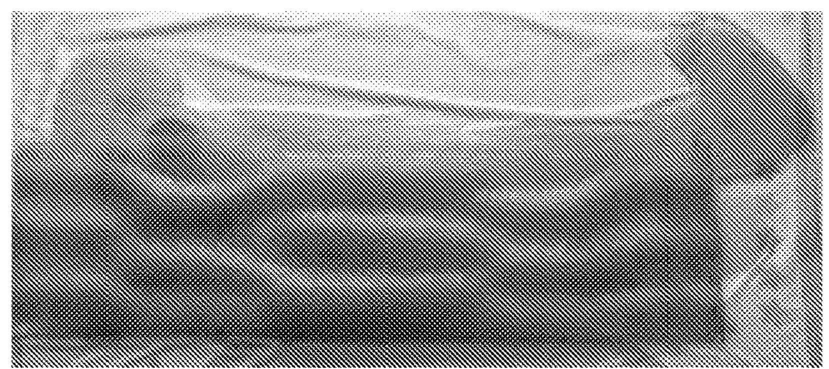
FIG. 8B is an exemplary embodiment of an absorbent article in accordance with the present disclosure. This absorbent article was made with the varied diamond pattern mask of FIG. 7B.
Figure 8C:
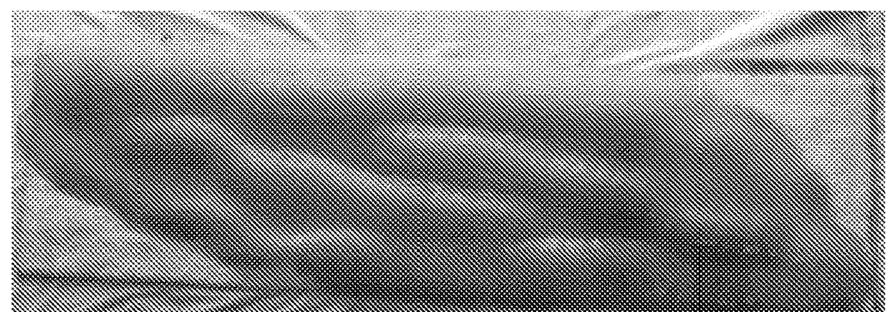
FIG. 8C is an exemplary embodiment of an absorbent article in accordance with the present disclosure. This absorbent article was made with the varied diamond pattern mask of FIG. 7C.
Figure 8D:
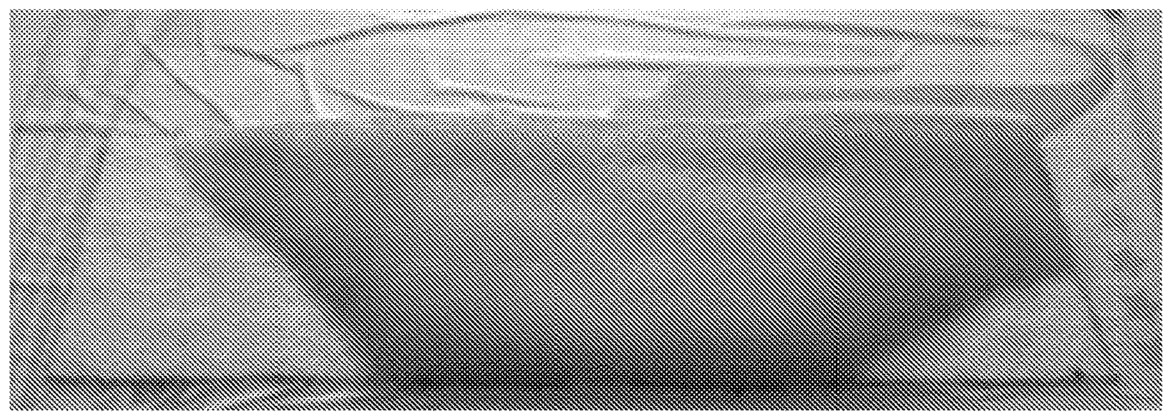
FIG. 8D is a control absorbent article not in accordance with the present disclosure. This absorbent article was made by applying uniform adhesive.

Mask 7A, indicated generally at 50, is shown in FIG. 7A. Mask 7A has 2.33" extended ellipses 52 (1" long rectangles with elliptical end caps) that are %" wide. The ellipses are separated in the CD by a CD gap 54 of ⅜". The center-to-center spacing in the MD 56 is 1.75" and is offset to form a hexagonal array. The negative space (hatched) is where adhesive was applied.

Mask 7B, indicated generally at 60, is shown in FIG. 7B. Mask 7B has rectangles 62 that are ⅜" wide and 2" long. The CD gap 64 is %". The MD gap 66 is 1", with the pattern staggered to form hexagonal array. The edge adhesive 68 is %".

Mask 7C, indicated generally at 70, is shown in FIG. 7C. Mask 7C has rectangles 72 that are ⅜" wide and 1" long. The CD gap 74 is 4". The MD gap 76 is 1", with the pattern staggered to form hexagonal array. The edge adhesive 78 is ½".

Mask 7A provides oval-shaped areas where the absorbent can swell, with the remainder of the material covered in adhesive, except for the vertical lines left for convenience in making the mask. Masks 7B and 7C are similar to Mask 5, but with extra adhesive at the edges. Mask 7C has the same line segments pattern as Mask 5, while Mask 7B has longer line segments, 2" instead of 1", compared to Mask 5.

FIG. 8 shows comparative results between FRODO materials patterned with Masks 7A-7C and a control example fully covered with adhesive. FIG. 8A shows a FRODO material patterned with Mask 7A after taking in 200 mL of saline over about 1 minute. FIG. 8B shows a FRODO material patterned with Mask 7B after taking in 200 mL of saline over about 30 seconds. FIG. 8C shows a FRODO material patterned with Mask 7C after taking in 150 mL of saline over about 40 seconds. FIG. 8D shows a FRODO material patterned with full adhesive after taking in 140 mL saline, much of which spilled out the top edge, over about 1 minute.

The FRODO materials patterned with Masks 7A-7C stayed essentially flat against the table during testing. However, the control arched up significantly. These differences could impact rigidity and conformability of absorbent composites containing these patterned materials.

Furthermore, before the superabsorbent was fully swollen, liquid was observed to flow through the valleys, and also to fill the void space beneath the ridges, for the FRODO materials patterned with Masks 7A-7C. This additional open space could help control fluid upon insult before it is absorbed in the superabsorbent material.

The FRODO material patterned with Mask 7A exhibited the best performance. The adhesive surrounding the buckling region initially kept the buckling controlled and the adhesive around the edges kept the overall shape intact.

In all cases, the patterns allowed directed fluid motion through the valleys and under the ridges. The patterns further moved fluid in the MD direction, thereby enabling better use of the absorbent capacity when flat. Patterned adhesive may also reduce the overall rigidity of swollen materials.

Example 7. High Pressure Intake Testing in Diapers

Testing in diapers was performed at high pressure to determine the conditions necessary for ridge formation.

A test diaper was made by replacing the SAM material of a diaper containing 50% SAM core with a patterned FRODO material. Freeze spray was used to remove some of the adhesive on the front and back of the diaper attaching the flaps to the chassis, and additional minimal freeze spray was used to disconnect the liner from the outer cover. During this process, it was ensured that the gasketing material was not separated from the chassis on the sides. Scissors were used to cut out the liner. After spraying Super77 adhesive through the Mask 7A patterned mask and attaching the FRODO core, strips of adhesive were used to reattach the flaps at front and back. The original liner and surge were reapplied only with adhesive strips around the outside of the FRODO material and front and back of it. There was no adhesive on top of the core.

A simple intake test was performed using a hi-lo rewet intake board. The intake board is a rectangular polycarbonate board (300 mm length and 100 mm width) that includes an open cylinder located in the central area of the plate. The internal diameter of the cylinder is 38 mm and the height is 125 mm. A test diaper is held open and flat (with Velcro tape) and the insult board is placed on top of it with the insult location 8.5 cm from the center of the diaper, in the direction of the front of the diaper. 85 mL of saline was measured and poured quickly into the open cylinder of the insult board. Intake time, measured with a stopwatch, starts as soon as fluid first hits the diaper and ends. Intake time ends as soon as the liquid passes completely through the cylinder and into the diaper, with no liquid being on the surface of the diaper.

Initially, 8 kg weights, corresponding to about 0.45 PSI, were on the diapers to visually determine if the patterns could create void space even under pressure. Intake under pressure was very slow. After several minutes, the weights were removed and the fluid finally went into the product. Controlled buckling never occurred, even after a second insult at low pressure.

There are several possible explanations why no features emerged. First, when the adhesive patterns were applied and the FRODO material was adhered to the core, the diaper was stretched in the MD, with no deliberate CD tension. Wrinkles in the MD could have allowed the core width to grow in the CD rather than present responsive topography. Second, the 8 kg weight on first insult may have forced swelling to occur in a different way than it would have otherwise. Finally, the adhesive over the core, which adhered the non-elastic liner to the core, may have constrained the surface area, thereby inhibiting in-plane swelling. In any case, no responsive channels or bumped formed under pressure.

Example 8. Low Pressure Intake Testing in Diapers

Testing in diapers was performed at low pressure to determine the conditions necessary for ridge formation.

The materials and procedures for the test diapers were the same as for Example 7. In addition to the diaper with the FRODO material patterned by Mask 7A, a control diaper was prepared with a FRODO material fully covered in adhesive Super77 adhesive.

The first intake time was fairly slow with FRODO absorbents. The responsive channels were not fast enough to impact the first intake time. However, bumps and channels were clear and visible after the first rewet test.

A second low pressure test was performed. Fluid entered the diaper essentially as fast as it could pour through the funnel. The low pressure intake and rewet data are in Table 2.

TABLE 2

Low pressure intake and rewet test results.

| Sample | First intake (s) | First rewet (g) | Second intake (s) |
|---|---|---|---|
| Unpatterned FRODO control | 50.56 | 0.453 | 52.06 |
| FRODO material patterned with Mask 7A | 45.81 | 0.526 | 6.96 |

After the two low pressure intakes, a board with weights was placed on the diaper, and the bumps were visibly flattened, thereby erasing the intake benefits of the responsive controlled swell. The bumps reappeared after removal of the weights.

The prepared diapers were compared after two 85 mL saline intakes. The FRODO control core was relatively flat and rigid, while the FRODO material patterned with Mask 7A core was much less rigid.

These results demonstrate that responsive bumps and channels lead to very fast intake second intake times under low pressure. Higher pressures flatten the bumps and erase the intake benefits until the pressure is removed. The pattern of Mask 7A greatly reduces the core stiffness.

Example 9. Patterns with Low Amounts of Adhesive

Additional masks were created by modifying the pattern of Mask 7A.

The materials and procedures were the same as for Examples 4 and 5. The masks are shown in FIGS. 9A-D.

The Mask 7A pattern was modified by shrinking the bumps in the MD direction to create more small bumps. Specifically, the 1" rectangular middle section of the extended ellipses in Mask 7A was removed to leave only the elliptical end caps. Further, the side edge was rippled.

Mask 9A, indicated generally at 80, is shown in FIG. 9A. The ellipses 82 are separated by a CD gap 84 and a MD gap 86. The MD length is 1.33" and the width is 0.74".

In addition, a corresponding top side mask (Mask 9B) was drawn, for applying adhesive (in the black spots) between the core and the liner/surge at the location of the peaks. Mask 9B, indicated generally at 90, is shown in FIG. 9B. The ellipses 92 are separated by a CD gap 94 and a MD gap 96.

A linear mask pattern (Mask 9C) was made similar to the Mask 3C pattern; it contained adhesive stripes at the edges and down the center beneath the core. Mask 9C, indicated generally at 100, is shown in FIG. 9C. The rectangles 102 are separated by a CD gap 104. Adhesive stripes 106 are at the edges and down the center beneath the core. The adhesive width is 0.5" at the edges and ⅜" in the center. The adhesive width at the MD extremes is ⅞".

A corresponding top side mask (Mask 9D) was drawn with two stripes above the core to correspond to where the peaks of the ridges would occur. Mask 9D, indicated generally at 110, is shown in FIG. 9D. The rectangles 112 are separated by a CD gap 114. The line/rectangle width is 0.3" and the length is 11.5". The squares at the corners 116 are present for the practical purpose of mask alignment.

Example 10. Low and High Pressure Intake Testing in Diapers

Testing in diapers was performed at low and high pressure to determine the effect of adhesive coverage.

The materials and procedures for the test diapers were the same as for Example 7.

The intake and rewet data are in Table 3. The first intake and rewet were at low pressure, about 0.009 PSI, and the second intake and rewet were at high pressure, about 0.45 PSI.

TABLE 3

| Intake and rewet test results. | | | | |
|---|---|---|---|---|
| Sample | First intake (s) | First rewet (g) | Second intake (s) | Second rewet (g) |
| Unpatterned FRODO control | 53 | 0.40 | 450 | 15.48 |
| FRODO material patterned with Mask 9C | 37 | 0.74 | 452 | 11.95 |
| FRODO material patterned with Mask 9A | 41 | 0.58 | 324 | 8 |

Channels and bumps were clearly visible after the first intake. For the FRODO material patterned with Mask 9A, the adhesive between bumps did not always hold and bumps tended to be connected into random channels.

Under pressure, the second intake was not dramatically reduced because the bumps and channels were flattened. The bumps reappeared after removing the weight.

After the second rewet test, the relatively thin strips of adhesive in the patterned FRODO materials did not hold, and the result was a loose SAM mass wrinkled and folded in on itself. More adhesive coverage is needed than provided in these masks. In contrast, the control was reasonably well attached to the outer cover.

Rewet was lowered by the patterns, likely because the pressure predominantly falls on the top of the ridges, even if the ridges are largely pressed down, thereby preventing fluid channeling.

Example 11. Patterns with High Amounts of Adhesive

Additional masks were created by modifying the pattern of Mask 7A.

The materials and procedures were the same as for Examples 4 and 5. The masks are shown in FIGS. 10A-B.

The Mask 7A pattern was modified by separating the bumps in the MD direction, tapering the ends, and slightly shrinking the CD width, to allow for more adhesive between bumps. The resulting pattern is referred to as Mask 10A.

Figures 10A, 10B:
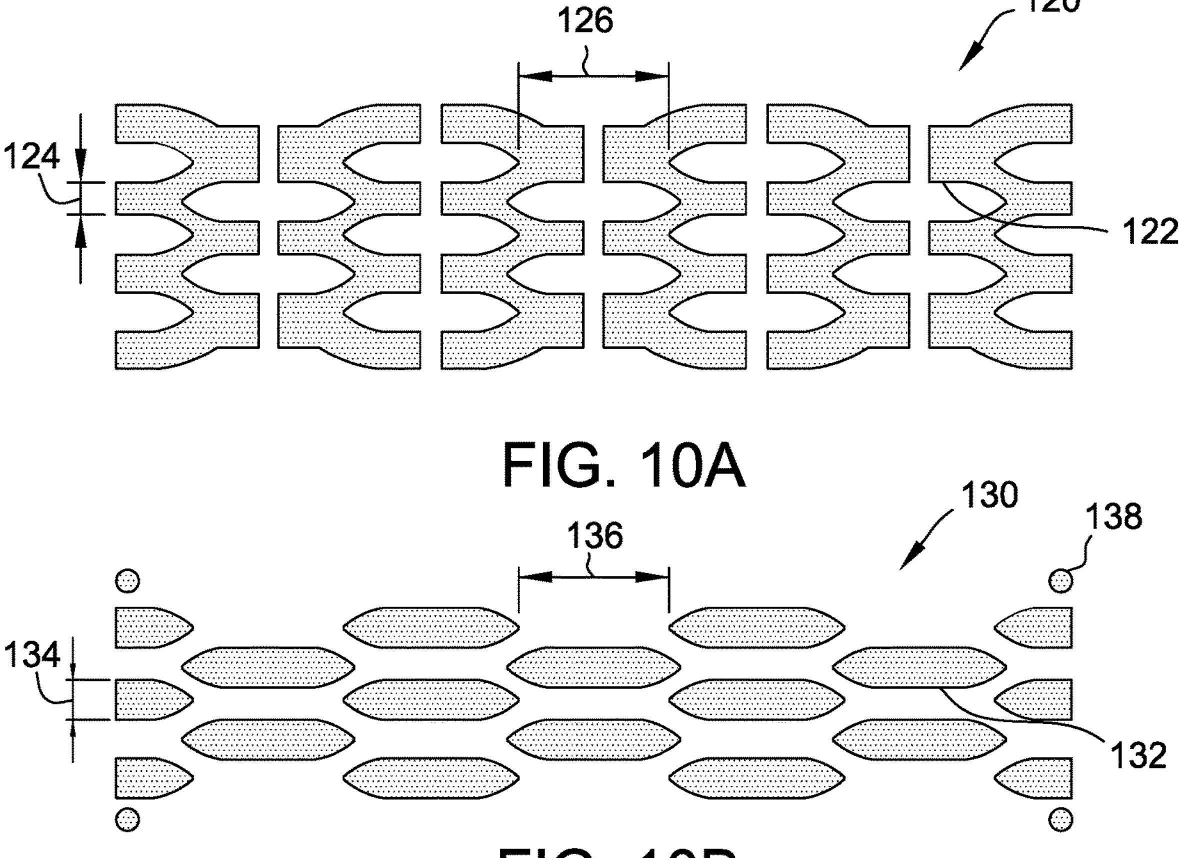
FIG. 10A is an exemplary embodiment of a pattern mask in accordance with the present disclosure that was prepared by modifying the pattern mask of FIG. 7A.
FIG. 10B is an exemplary embodiment of a top side mask in accordance with the present disclosure for applying adhesive in the pattern mask of FIG. 10A.

Mask 10A, indicated generally at 120, is shown in FIG. 10A. The ellipses 122 are separated by a CD gap 124 and a MD gap 126. The bump width is ⅝". The adhesive width in the CD direction is ½" between bumps. The minimum adhesive width between bumps (i.e. where the 2-bump and 3-bump rows come together) is 0.31". The adhesive width is 0.56" at the edges where there are 3 bumps in a row, or 0.81" at the edges where there are just 2 bumps. The bump length is 2.66".

In addition, a corresponding top side mask (Mask 10B) was drawn, for applying adhesive (in the black spots) between the core and the liner/surge at the location of the peaks.

Mask 10B, indicated generally at 130, is shown in FIG. 10B. The ellipses 132 are separated by a CD gap 134 and a MD gap 136. The feature width is 0.47" and the length is 2.0". Again, the squares at the corners 138 are for the practical purpose of mask alignment.

Example 12. High Pressure Intake Testing in Diapers

Testing in diapers was performed at low and high pressure to determine the effect of adhesive coverage.

The materials and procedures for the test diapers were the same as for Example 7.

The intake and rewet data are in Table 4. The first intake and rewet were at low pressure and the second intake and rewet were at high pressure.

TABLE 4

| Intake and rewet test results. | | | | |
|---|---|---|---|---|
| Sample | First intake (s) | First rewet (g) | Second intake (s) | Second rewet(g) |
| Unpatterned FRODO control | 43.1 | 0.547 | 429.89 | 15.438 |
| FRODO material patterned with Mask 10A | 38.75 | 0.847 | 382.88 | 15.463 |

Channels and bumps were clearly visible after the first intake, although smaller than the FRODO materials patterned with Mask 7A.

Under pressure, the second intake was not dramatically reduced because the bumps and channels were flattened. The bumps reappeared after removing the weight.

The adhesive held well except at the edges, where the parts of the core that were not glued down curled up and caused stress on the adhesive, thereby causing failure at edge points. The curled edges also did not improve the feel relative to hard edges. However, side compressibility was reduced.

Example 13. Patterns with Long Strips of Adhesive

Additional masks were created to prevent the core from curling up on the sides.

Figures 11A, 11B:
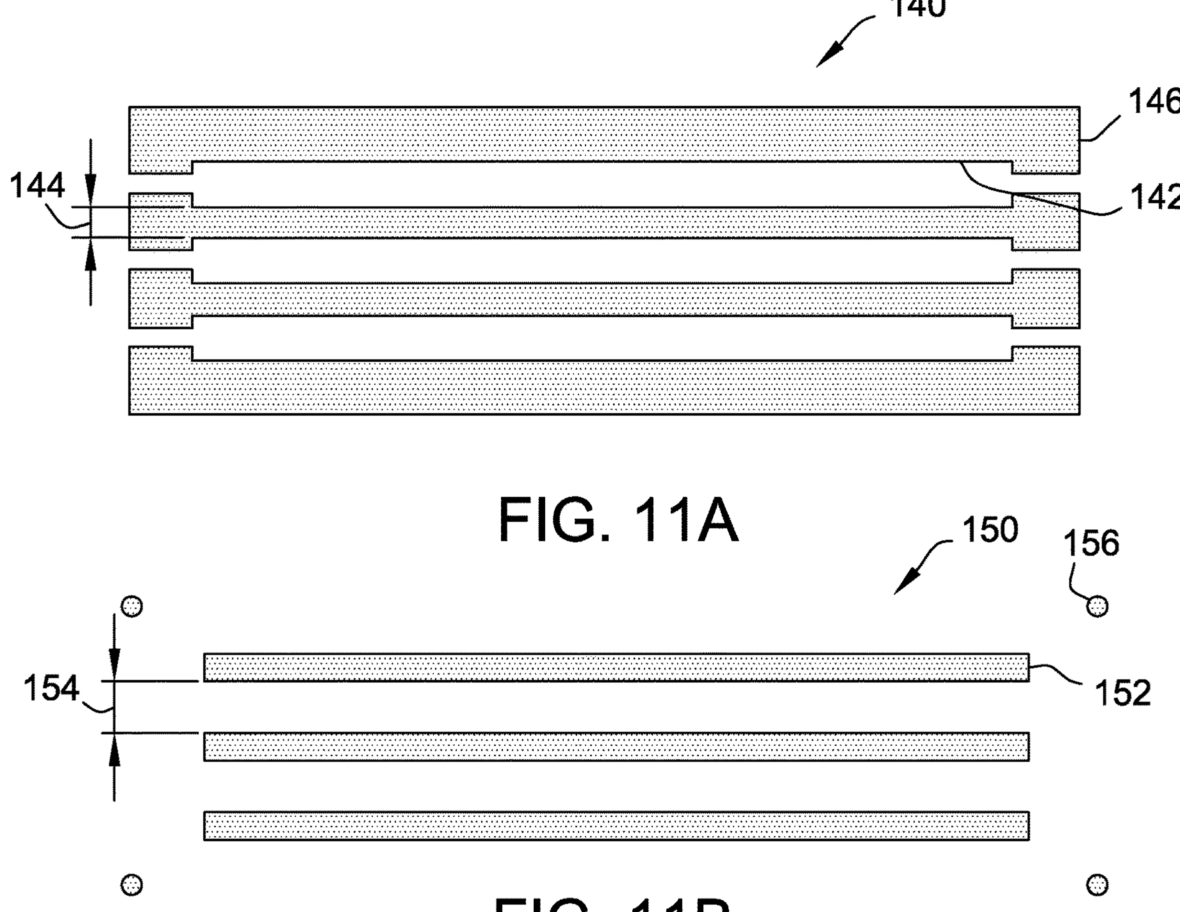
FIG. 11A is an exemplary embodiment of a pattern mask in accordance with the present disclosure that was prepared by modifying the pattern mask of FIG. 3C.
FIG. 11B is an exemplary embodiment of a top side mask in accordance with the present disclosure for applying adhesive in the pattern mask of FIG. 11A.

The materials and procedures were the same as for Examples 4 and 5. The masks are shown in FIGS. 11A-B.

A linear mask pattern (Mask 11A) was made similar to the Mask 3C pattern; it contained adhesive stripes at the edges and down the center beneath the core. Mask 11A, indicated generally at 140, is shown in FIG. 11A. The rectangles 142 are separated by a CD gap 144. Adhesive stripes 146 are at the edges and down the center beneath the core. Mask 11A has four strips of adhesive instead of three, and the adhesive strips are thicker. The inner adhesive strips are 0.5" wide. The CD edges are 0.81" wide. The MD ends are 1" wide.

A corresponding top side mask (Mask 11B) was drawn for applying adhesive between the core and the liner/surge at the location of the peaks. Mask 11B, indicated generally at 150, is shown in FIG. 11B. The rectangles 152 are separated by a CD gap 154. The three adhesive strips 152 are each 0.43" by 12". The squares at the corners 156 are present for the practical purpose of mask alignment.

Example 10. Low Pressure Intake Testing in Diapers

Testing in diapers was performed at low pressure to determine the effect of adhesive coverage.

The materials and procedures for the test diapers were the same as for Example 7.

The intake and rewet data are in Table 5. The intakes and rewet were at low pressure.

TABLE 5

Intake and rewet test results.

| Sample | First intake (s) | First rewet (g) | Second intake (s) |
|---|---|---|---|
| Unpatterned FRODO control | 50.56 | 0.453 | 52.06 |
| FRODO material patterned with Mask 11A | 44.24 | 0.339 | 9.51 |

Channels and bumps were clearly visible after the first intake within one minute. The channels could support up to 0.17 PSI (2886 g of weight) on the intake board but collapsed under 0.23 PSI (3971 g).

The diapers were handled about 5 minutes after the second intake. The side compressibility was good, but the hard edge was still present. After about 30 seconds, the inner adhesive failed. The core became very floppy, although soft in the CD. When the ridges stick up, any compression from above or pressure from the side put stress on the adhesive, thereby causing adhesive failure.

The diapers performed well for second intake at low pressure.

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises," "comprising," "includes." "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

What is claimed is:

1. An absorbent article comprising:

an absorbent core comprising a superabsorbent material; and a stability layer;

wherein the absorbent core is heterogeneously attached to the stability layer;

wherein upon wetting, the absorbent core swells in a lateral direction by at least about 20% such that the wetted absorbent core presents a responsive topography feature in a location where the absorbent core is not heterogeneously attached to the stability layer, wherein the swelling is such that the absorbent core is not in contact with the stability layer at locations where the absorbent core is not attached to the stability layer; and wherein the lateral direction is a cross machine direction.

2. The absorbent article of claim 1, wherein the stability layer is selected from the group consisting of a liquid impervious backsheet, a spacer layer, a spunbond spacer layer, a nonwoven material, a film, and combinations thereof.

3. The absorbent article of claim 1, wherein the absorbent core is heterogeneously attached to the stability layer according to a pattern comprising features selected from the group consisting of circles, ovals, squares, rectangles, triangles, diamonds, geometric shapes, modified geometric shapes, asymmetric shapes, shapes created in a negative space between a plurality of features, strips, stripes, ripples, and combinations thereof.

4. The absorbent article of claim 1, wherein at least two of the features are connected to a degree selected from the group consisting of fully connected, partially connected, and not connected.

5. The absorbent article of claim 1, wherein the absorbent core comprises a material selected from the group consisting of a stabilized superabsorbent material, a superabsorbent material bound in a nonwoven web, a FRODO material, a coform superabsorbent material, a superabsorbent airlaid, a superabsorbent foam, a superabsorbent material laminated to a nonwoven facing that is stretchable in-plane, and combinations thereof.

6. The absorbent article of claim 1, wherein upon wetting, the absorbent core swells in a lateral direction and in a non-lateral direction.

7. The absorbent article of claim 1, wherein the absorbent core further swells by at least about 20% in a machine direction.

8. The absorbent article of claim 1, wherein the absorbent core presents a responsive topography feature within about 15 seconds of wetting.

9. The absorbent article of claim 1, wherein the absorbent core presents a responsive topography feature with a height in the range of from about 5 mm to about 25 mm.

10. The absorbent article of claim 1, wherein the absorbent core presents a responsive topography feature with a height in the range of from about 10 mm to about 20 mm.

11. The absorbent article of claim 1, wherein the responsive topography feature is selected from the group consisting of hills, ridges, bumps, dots, channels, voids, valleys, drumlins, eskers, and combinations thereof.

12. The absorbent article of claim 1, wherein the responsive topography feature enhances distribution of fluid through the responsive absorbent material.

13. The absorbent article of claim 1, wherein the responsive topography feature reduces intake time during an insult subsequent to a first insult.

14. The absorbent article of claim 1, wherein the stability layer comprises a material selected from the group consisting of a polymer, polyethylene, a plastic, a thin plastic film, a flexible liquid-impermeable material, a polymer-wood fiber composite, a tissue-based structure, and combinations thereof.

15. The absorbent article of claim 1, wherein the absorbent article is substantially flexible before wetting and substantially rigid after wetting.

16. A method of producing an absorbent article comprising:
- an absorbent core comprising a superabsorbent material; and
- a stability layer;
- wherein the absorbent core is heterogeneously attached to the stability layer;
- wherein upon wetting, the absorbent core swells in a lateral direction by at least about 20% such that the wetted absorbent core presents a responsive topography feature in a location where the absorbent core is not heterogeneously attached to the stability layer, wherein the swelling is such that the absorbent core is not in contact with the stability layer at locations where the absorbent core is not attached to the stability layer; and
- wherein the lateral direction is a cross machine direction,
- the method comprising:
- heterogeneously coupling the absorbent core to the stability layer.

17. The method of claim 16, wherein the method step of heterogeneously coupling the absorbent core to the stability layer comprises forming a bond selected from the group consisting of adhesive bonds, sonic bonds, thermal bonds, and combinations thereof.

18. The method of claim 16, wherein the stability layer is selected from the group consisting of a liquid impervious backsheet, a spacer layer, a spunbond spacer layer, a nonwoven material, a film, and combinations thereof.

19. A method of using an absorbent article comprising:
- an absorbent core comprising a superabsorbent material; and
- a stability layer;
- wherein the absorbent core is heterogeneously attached to the stability layer;
- wherein upon wetting, the absorbent core swells by at least about 20% in a lateral direction such that the wetted absorbent core presents a responsive topography feature in a location where the absorbent core is not heterogeneously attached to the stability layer, wherein the swelling is such that the absorbent core is not in contact with the stability layer at locations where the absorbent core is not attached to the stability layer; and
- wherein the lateral direction is a cross machine direction,
- the method comprising using the absorbent article in a consumer product.

20. The method of claim 19, wherein the consumer product is selected from the group consisting of cloth products, diapers, potty training pants, feminine napkins, adult incontinence pads, adult incontinence garments, and disposable bed liners.

* * * * *